United States Patent
Robison et al.

(10) Patent No.: US 6,824,552 B2
(45) Date of Patent: Nov. 30, 2004

(54) SURGICAL CUTTING ACCESSORY WITH NICKEL TITANIUM ALLOY CUTTING HEAD

(75) Inventors: Braden M. Robison, Fremont, CA (US); Nathan A. Swain, Sunnyvale, CA (US)

(73) Assignee: Stryker Corporation, Kalamazoo, MI (US)

( * ) Notice: Subject to any disclaimer, the term of this patent is extended or adjusted under 35 U.S.C. 154(b) by 84 days.

(21) Appl. No.: 10/115,607

(22) Filed: Apr. 3, 2002

(65) Prior Publication Data

US 2003/0191487 A1 Oct. 9, 2003

(51) Int. Cl.[7] .............................................. A61B 17/32
(52) U.S. Cl. ..................................... 606/170; 606/79
(58) Field of Search ........................... 606/96, 80, 170, 606/180, 159, 79, 84, 167; 433/165; 407/30, 32, 36–40; 408/127

(56) References Cited

U.S. PATENT DOCUMENTS

| | | | | |
|---|---|---|---|---|
| 4,297,597 A | * | 10/1981 | Kimura | 327/575 |
| 5,030,201 A | * | 7/1991 | Palestrant | 604/22 |
| 5,318,576 A | * | 6/1994 | Plassche et al. | 606/159 |
| 5,330,468 A | | 7/1994 | Burkhart | |
| 5,667,509 A | | 9/1997 | Westin | |
| 5,882,198 A | * | 3/1999 | Taylor et al. | 433/102 |
| 5,915,964 A | * | 6/1999 | Walia | 433/102 |
| 5,967,997 A | | 10/1999 | Turturro et al. | |
| 6,213,771 B1 | * | 4/2001 | Fischer | 433/75 |
| 6,214,016 B1 | * | 4/2001 | Williams et al. | 606/108 |
| 6,564,806 B1 | * | 5/2003 | Fogarty et al. | 128/899 |
| 2002/0058551 A1 | * | 5/2002 | White | 464/89 |
| 2003/0077553 A1 | * | 4/2003 | Brock | 433/102 |

OTHER PUBLICATIONS

VIRTECHS, Endodontics.*
Noguera, Angela P. et al., "Latest Technology".*

* cited by examiner

Primary Examiner—David O. Reip
Assistant Examiner—D. Jacob Davis
(74) Attorney, Agent, or Firm—Flynn, Thiel, Boutell & Tanis, P.C.

(57) ABSTRACT

A cutting accessory (20) for use with powered surgical tools. The cutting accessory has a hub (28) for coupling the accessory to the output shaft of a handpiece. A drive shaft (26) formed of stainless steel or other relatively rigid material extends forward from the hub. A head (30) formed from nickel titanium alloy or other metal that is more flexible than the material forming the drive shaft is attached to the distal end of the drive shaft. The head is shaped to form the cutting edges of the cutting accessory. In some versions of the invention, intermediate sections (60) of the drive shaft are formed from the flexible metal or metal alloy.

43 Claims, 5 Drawing Sheets

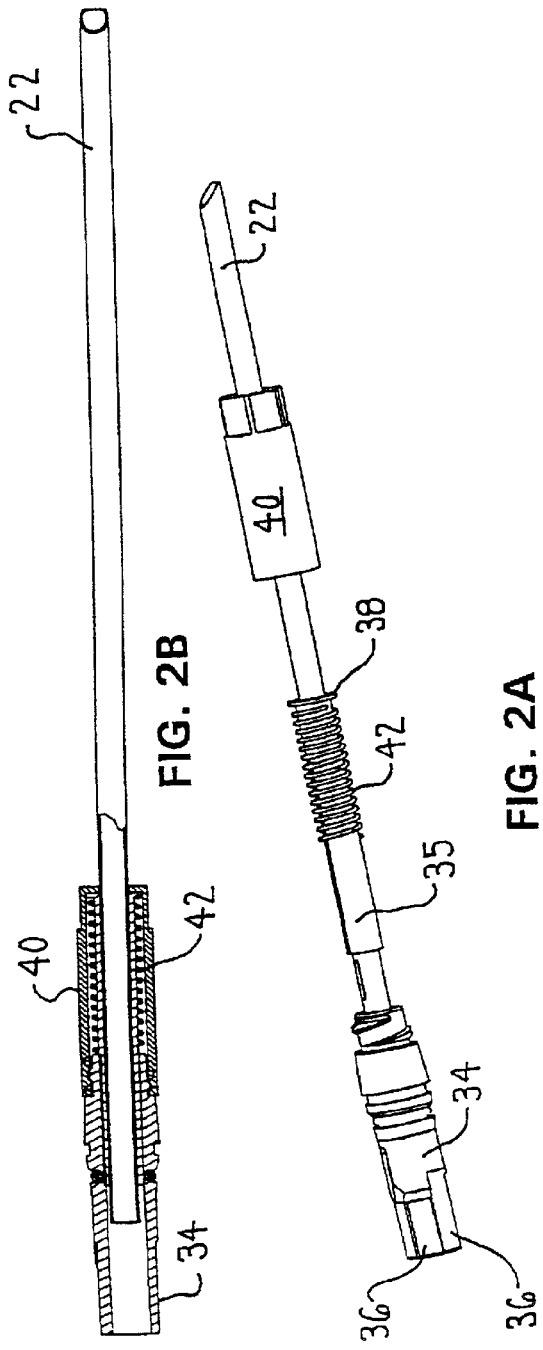

SURGICAL CUTTING ACCESSORY WITH NICKEL TITANIUM ALLOY CUTTING HEAD

FIELD OF THE INVENTION

This invention relates generally to a surgical cutting accessory that is used to cut tissue and, more particularly, to a surgical cutting accessory with a nickel titanium alloy cutting head.

BACKGROUND OF THE INVENTION

One component that is an integral part of many surgical tool systems is the cutting accessory. This cutting accessory is a device that is typically attached to some sort of driving unit. Often, but not always, the driving unit is some type of handpiece that contains an electrically or pneumatically driven motor. The cutting accessory is an elongated member that extends from the handpiece. The distal end of the cutting accessory, the end furthest from the surgeon, is shaped to define a cutting head. In order to remove tissue, the surgeon actuates the handpiece and applies the cutting head of the accessory to the tissue to be removed. If the tissue being cut is bone, the cutting head is used to form a bore in the bone or to otherwise shape the bone.

Often cutting accessories are fabricated from stainless steel. Advantages of making an accessory out of this material are that it is relatively economical to provide, the steel can be shaped to define the sharp cutting surfaces of the head, and it can also withstand the rigors of post manufacture sterilization without physical degradation.

Nevertheless, there are some disadvantages associated with providing cutting accessories with cutting heads formed from steel. Specifically, steel is relatively rigid. Consequently, when a cutting accessory with a steel head is pressed against bone, the surgeon may have to precisely hold the accessory against the bone so that it does not bend significantly relative to the longitudinal axis of the bore being formed. If there is significant deviation from this axis, the cutting head may not be able to withstand the stress.

SUMMARY OF THE INVENTION

This invention relates to a new and useful surgical cutting accessory. In one version of the cutting accessory of this invention, the accessory is provided with a shaft formed from stainless steel and a head formed from a metal that has more flexibility than the stainless steel. In some preferred versions of this invention, the material from which the head is formed is a nickel titanium alloy. This head may be a drill tip, a bur head or open ended tubular member that forms part of a tissue cutter. In alternative versions of this invention, the whole of the cutting accessory, its shaft and head, are formed from material that has a greater degree of flexibility than stainless steel.

In still other alternative versions of the invention, a cutting accessory may have a shaft that comprises one or more sections of rigid material like stainless steel and one or more sections of a more flexible metal or metal alloy such as the nickel titanium alloy. In some embodiments of these versions of the invention, the shaft is formed substantially of steel, has a distal end neck formed of the more flexible metal or metal alloy and a cutting head formed of steel.

BRIEF DESCRIPTION OF THE DRAWINGS

The invention is pointed out with particularity in the claims. The above, and further features and advantages of the invention, are understood by reference to the drawings in which:

FIG. 1 is a plan and partially cutaway view of a surgical cutting accessory of this invention;

FIG. 2A is an exploded view of a cutting accessory;

FIG. 2B is a plan and partially cutaway view of the outer tube of the cutting accessory;

DETAILED DESCRIPTION

Figure 3:
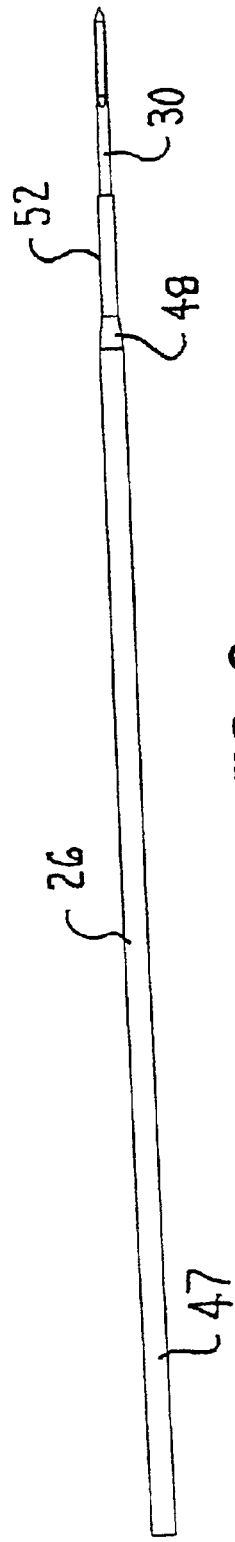
FIG. 3 is a plan view of the drive shaft and head of the cutting accessory.

FIGS. 1, 2A and 2B illustrate one surgical cutting accessory 20 of this invention. The particular accessory is a subchondral drill used to cut holes in bone that is surrounded by soft tissue. This particular type of drill is designed for use in an endoscopic surgical procedure in which its elongated body is inserted into a portal formed in the body of the patient. It should be understood that other cutting accessories are designed to perform other types of surgical procedures, including non-endoscopic, open cut procedures.

The depicted cutting accessory 20 has an outer tube 22 that, in this version of the cutting accessory, is sometimes referred to as a retractable housing. The proximal end of the outer tube 22, the end opposite the distal end, is coupled to an outer hub assembly 24. The outer hub assembly 24 is used to releasably hold the cutting accessory 20 to the handpiece with which it is used, (handpiece not illustrated). One such handpiece is sold by the Applicants' Assignee under the trademark TPS 12K Shaver. Located within, and extending axially through outer tube 22 and outer hub assembly 24, is a tubular drive shaft 26. An inner hub 28 is attached to the proximal end of the drive shaft that extends out of the outer hub assembly 24. The inner hub assembly is shaped to releasably engage with a motor coupling that is connected to the motor drive shaft that is part of the handpiece with which the cutting accessory 20 is used. This inner hub 28 is coupled to the handpiece so as to transfer the rotational movement of the handpiece drive shaft to the accessory drive shaft 26. It should, of course, be recognized that this rotational movement may not, at all times, be unidirectional. Some cutting accessories, in some or all surgical procedures, are driven in an oscillatory movement pattern by the complementary handpiece in order to perform the desired surgical procedure.

A head 30 is attached to the distal end of the drive shaft 26. Head 30 is the portion of the cutting accessory 20 that performs the tissue removal function.

In the depicted version of the invention, the outer hub assembly 24 is provided with a head piece 34 that is the most proximal portion of the outer hub assembly. The proximal end of head piece 34 is formed with surfaces 36 against which coupling members integral with the handpiece bear. It should be understood that the actual surface geometries of the inner hub 28 and the head piece 34 are a function of the coupling assembly integral with the handpiece with which the cutting accessory 20 is used. Exemplary surface geometries for these components are described and illustrated in the Applicants' Assignee's U.S. Pat. No. : 5,192,292, SUR- GICAL APPARATUS USEABLE FOR ARTHROSCOPIC SURGERY, issued Mar. 9, 1993; U.S. Pat. Nos. 5,690,660, ARTHROSCOPIC CUTTER HAVING CURVED ROTATABLE DRIVE, issued Nov. 25, 1997; and U.S. Pat. No. 6,007,556, SURGICAL IRRIGATION PUMP AND TOOL SYSTEM, issued 28, Dec. 1999, each of which is incorporated herein by reference. Again, it should be understood that these surface geometries are only exemplary and not limiting; the actual shape of the outer hub assembly 24 and inner hub 28 will be a function of the handpiece with which the cutting accessory 20 is used.

The proximal end of the outer tube 22 is slidably disposed within the headpiece 34. More particularly, as seen by FIGS. 2A and 2B, a collar 35 is fitted around the outer tube so as to extend forward from a position located forward of the proximal end of the tube. Collar 35 is the actual component that slidably abuts the inner wall, of head piece 34. Collar 35 is further formed to define an annular lip 38 around its distal end.

The portion of the collar 35 that extends forward from the distal end of head piece 34 is encased within a cylindrical shell 40 also part of the outer hub assembly. Shell 40 is secured to head piece 34. A coil spring 42 is disposed in shell 40 and extends around collar 35. One end of spring 42 bears against the ring-shaped, distally directed face of the head piece 34. The opposed end of spring 42 seats against collar lip 38. Spring 42 thus places a force on the collar 35 and outer tube 22 so as to push these components outwardly, away from head piece 34.

Inner hub 28, as discussed above, is shaped to engage with the drive integral with the handpiece with which the cutting accessory 20 is used. The inner hub is also shaped to have a port 37 that is in communication with the center bore that extends axially through the drive shaft 26. Typically, the handpiece with which the cutting accessory 20 is used has a bore that extends from the opening in which the accessory hubs 24 and 28 are seated. A suction is drawn through this bore from a pump external to the handpiece so as to draw a suction through the drive shaft 26.

Figure 4:
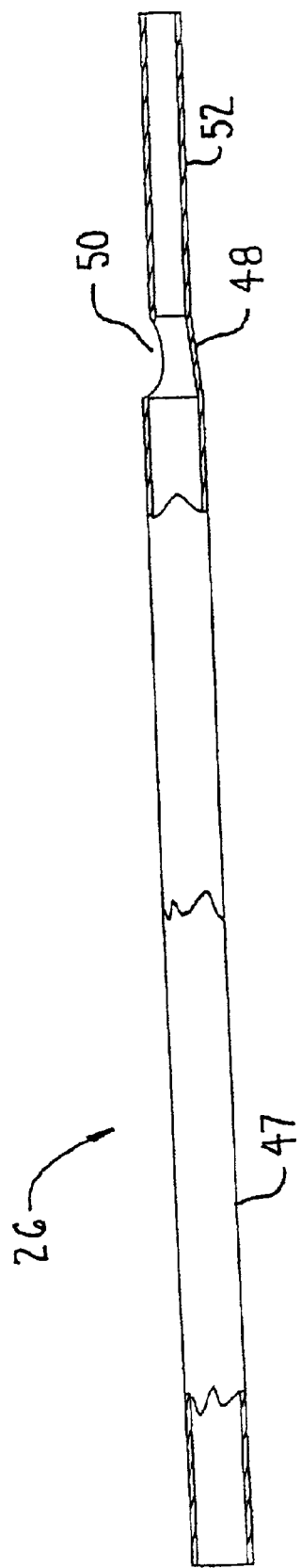
FIG. 4 is a cross-sectional view of the drive shaft.

In the depicted version of the invention, drive shaft 26, as seen in FIGS. 3 and 4, is formed so as to have a constant diameter main section 47 that comprises approximately 60 to 90% the total length of the shaft. In more preferred versions, main section 47 comprises between 70 to 80% of the overall length of the shaft. After the constant diameter main section 47, the drive shaft has an inwardly tapered section 48. An opening 50 is formed in tapered section 48. Opening 50 is the port in the cutting accessory through which fluid and debris at the surgical site are drawn into the drive shaft 26. Drive shaft 26 is further formed so as to have a constant diameter neck 52 that extends forward from the distal end of tapered section 26. In preferred versions of the invention, drive shaft 26 is manufactured from stainless steel. One type of stainless steel from which the drive shaft may be manufactured is 300 Series stainless steel. In some versions of the invention, 304 Series stainless steel has proven to be a suitable material for forming the drive shaft 26.

The drive shaft may be shaped to form the tapered section 48 and neck 52 by a swaging process. In some versions of the invention, the drive shaft 26 main section 47 has an outer diameter of 0.080 to 0.250 inches and a wall thickness of 0.005 to 0.030 inches. For example, some versions of the invention are further formed so that the drive shaft main section has an outer diameter of between 0.10 and 0.15 inches and a wall thickness of between 0.010 and 0.015 inches. It should also be understood that the metal or metal alloy from which the drive shaft is formed is relatively inflexible, for example, a metal or metal alloy that, when exposed to 1% or more strain, experiences plastic deformation.

Head 30 is seated in the open end of drive shaft neck 52. The head is formed from a material that has a greater degree of flexibility than the material forming the drive shaft. For example in some preferred versions of the invention, the head is formed from nickel titanium alloy. An alloy suitable for forming head 30 may be composed of the following materials by weight percent: nickel 54.5 to 57.0%; oxygen (max) 0.05%; carbon (max) 0.07%; and the remainder titanium. Often, this particular type of alloy is referred to as Nitinol. More generally, the metal or metal alloy from which the head is formed is of sufficient flexibility that even when it is exposed to at least 3% strain it will recover its initial shape. More preferred metals and metal alloys from which the head is formed are of sufficient flexibility that, when exposed to at least 5% strain, the head will recover its initial shape.

Figure 5:
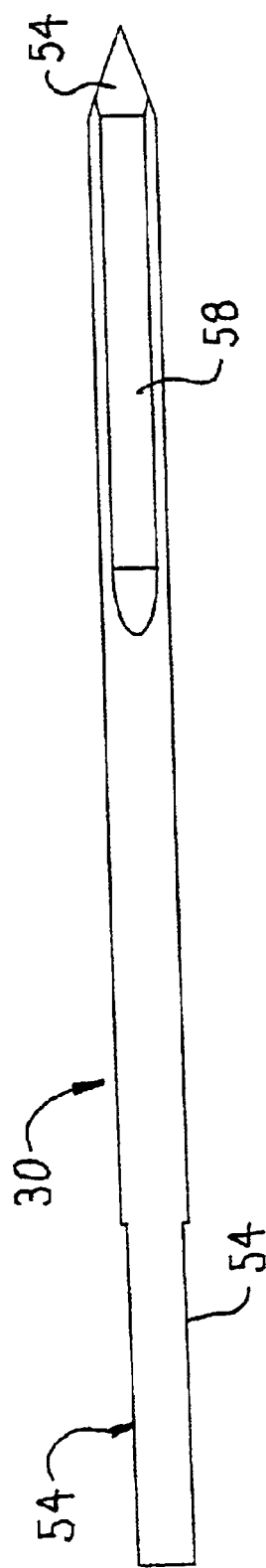
FIG. 5 is plan view of the cutting head of the inner tube.

Head 30 as seen in FIG. 5 is shaped to have a generally cylindrical shape. The head is further shaped to have opposed flats 54 that extend rearwardly from the proximally facing face of the head. The distal end 56 of the head, the tip of the head, is formed in the shape of a four-sided pyramid that meets at a point. Flats 58 extend from two of the opposed diametrically opposed sides of the pyramid a short distance proximally along the length of the head. The edges along which the sides of the pyramid 56 meet are the cutting edges of the head 30.

After the drive shaft 26 is formed, head 30 is seated in the open ended neck 52. The material forming neck 52 is pressed against the proximal end of the head to compression secure the head in place. The neck is pressed against flats 54 so as to prevent the head from rotating relative to the drive shaft 26.

The drive shaft-and-head subassembly is fitted in the outer hub-outer housing subassembly of FIG. 2B. In many versions of the invention, outer tube 22 and drive shaft 26 are dimensioned so that, absent any external force, the distal end of the outer tube just covers the distal end of the cutting head.

The described cutting accessory 20 is employed to bore a hole in hard tissue, bone. The accessory is used by pressing its distal end against the bone at the location at which the bore is to be formed. The handpiece to which the accessory is attached is actuated to cause the rotation of drive shaft 26 and head 30. The head 30 thus drills out the bone to form the desired hole. In this particular cutting accessory, the outer tube is disposed against the surface of the bone being cut. The outer tube 22 thus serves as a guard to prevent soft tissue from wrapping around the head 30 as the head is pressed into the bone. Owing to the telescoping relationship between the outer tube 22 and the outer hub assembly 24, the outer tube remains in a static position over the hole formed in the bone as the head 30 is pressed into the bone.

An advantage of the cutting accessory 20 of this invention is that the cutting accessory has a degree of flexibility at the location where it is needed, its distal end, its head end, and is otherwise relatively rigid. Thus, during surgery, when the head 30 is used to bore into bone, if the accessory 20 is angled so as to be offset from the longitudinal axis of the bone bore, since the head 30 is formed from a relatively flexible metal alloy, it will bend while in the bore. Since the head 30 bends, there is a significantly reduced likelihood that it or the drive shaft 26 will fail.

Still another advantage of this invention is that, if the cutting accessory 20 is subjected to side loading or bending when pressed against bone, the majority of the bending occurs in the head. Consequently, there is little, if any, bending of the shaft main section 47. This reduction in drive shaft bending reduces both the degree and frequency with which the bending of the drive shaft 26 is bent against the adjacent inner wall of the outer tube 22. The minimization of the drive shaft-against-outer tube contact reduces the instance in which such contact inhibits the rotation of the drive shaft 26.

Thus, the cutting accessory 20 of this invention is designed to flex at its distal end so as to not malfunction if angled while being used and to otherwise remain rigid so that the flexing does not adversely affect its use.

Still another advantage of the cutting accessory is that only a relatively small portion of the accessory is formed from the relatively expensive nickel titanium alloy. Thus, the cutting accessory of this invention is not appreciably more expensive than other cutting accessories.

It should be realized that the foregoing description is directed to one particular cutting accessory of this invention. Other versions of this invention may have features that are different from the described cutting accessory. For example, in some versions of the invention, the head may not be simply formed to function as a bore-forming drill. In some versions of the invention, the head may be formed to have a stem with a first diameter. This is the portion of the head that is secured to the drive shaft 26. Extending distally from the stem, the head 30 is formed to have a head member that has a second diameter that is greater than that of the stem. This head member has either a spherical or barrel shape. The head member is formed to have a number of different cutting edges and thus functions as a bur. These burs are designed to selectively remove tissue against which they are pressed.

Also, there is no requirement that all versions of the invention be constructed as drills or burs. In some versions of the invention, the head may be shaped to form part of a cutter. That is, the head is in the form of a tube that is closed at its distal end that, proximally to the closed distal end, has a window that is defined by sharp edges of the material forming the head. The outer tubes of the cutting accessories of these versions of the invention are formed with similar closed distal ends and adjacent windows. The edges of the rotating cutting head cooperate with similarly sharp edges of the static outer tube to function as scissors that separate the tissue against which the distal end of the cutting accessory is pressed. The separated tissue is drawn by suction away from the surgical site through the window formed in the rotating cutting head and the hollow center space within the complementary drive shaft. In these, as well as other versions of the invention, it should be understood that the drive shaft of the cutting accessory may have constant outer diameter along the whole of its length.

For example, while the described cutting accessory 20 is designed as a single use disposable cutting accessory, other cutting accessories may be designed to withstand the rigors of sterilization so that they can be used in multiple surgical procedures.

While one particular head 30 has been illustrated and described, other versions of the cutting accessory of this invention may have heads with different geometries. For example, other heads may not have the described pyramidal shaped distal end. The ends of these heads could be rounded. Similarly, grooves may be formed in the heads to provide pathways for the material removed by the cutting edges of the heads to travel out of the bore being formed. Also, it should be recognized that the number of cutting edges with which the head is provided might vary from what has been described. Furthermore, there is no requirement that, in all versions of the invention the cutting edges have a linear shape. In still other versions of the invention, these cutting edges may have curved, spiral or helical shapes.

Figure 6:
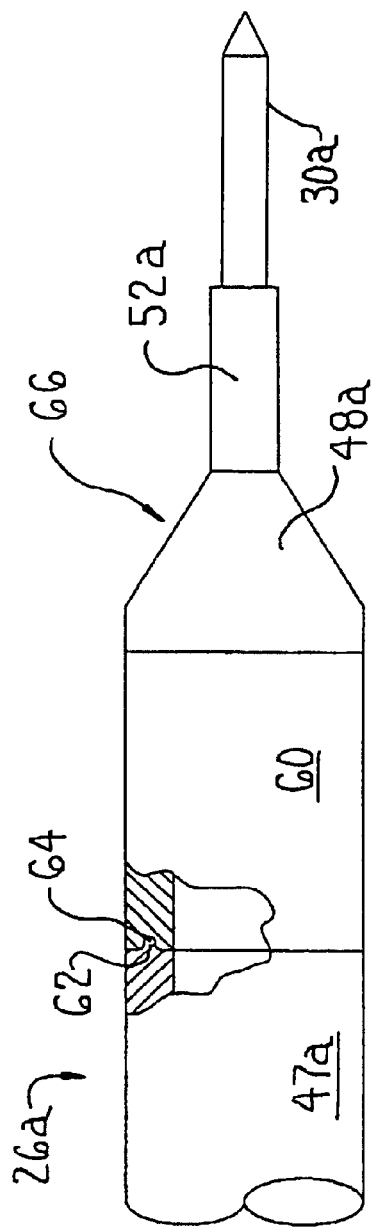
FIG. 6 is a side and partial cross-sectional view of an alternative drive shaft of this invention.
Figure 7:
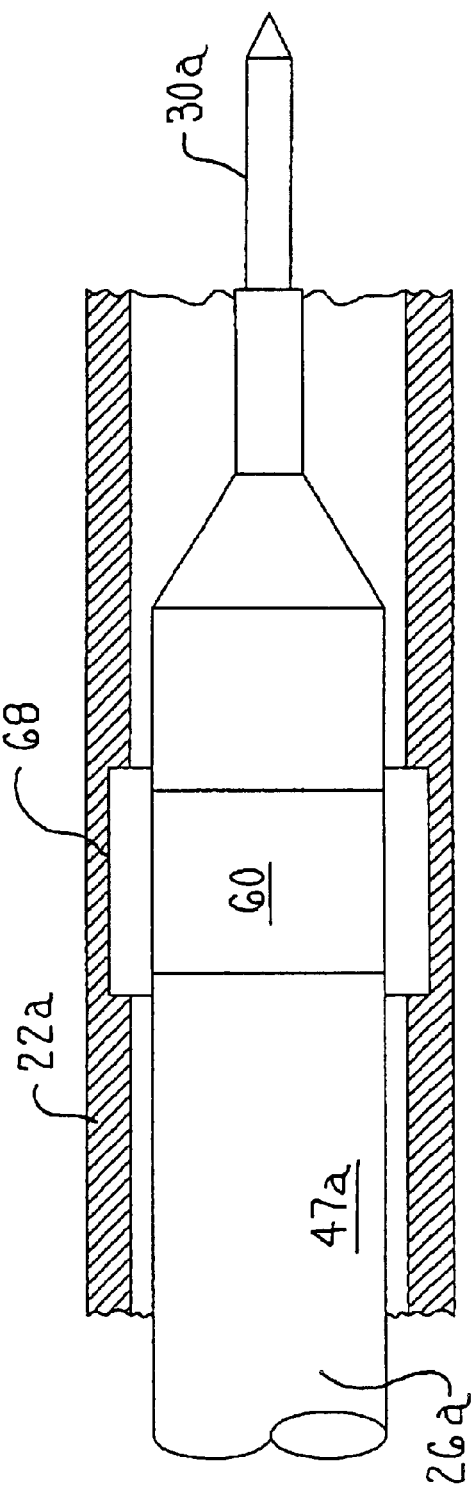
FIG. 7 is a side view depicting how the drive shaft of FIG. 6 is seated in an outer tube, the outer tube being shown in cross-section.

In still other versions of the invention, the material of increased flexibility is not located at the head. FIGS. 6 and 7 illustrate one such version of this invention. Here, the drive shaft 26a has a main section 47a formed of stainless steel. A tubular member 60 formed from the more flexible Nitinol is secured to the distal end of main section 47a. In order to facilitate the mating of these two components, the distal end of the main section 47a has a small forward facing lip 62 that seats in a circumferential groove 64 formed around the proximal facing face of member 60 adjacent the inner wall of the shoulder section. The components 47a and 60 are then joined together.

A shoulder section 66 formed from stainless steel extends forward from tubular member 60. Shoulder section 66 is shaped to define tapered section 48a and neck 52a. A head 30a formed of stainless steel extends forward from neck 52a. A lip-in-groove assembly similar to that used to secure member 60 to main section 47a is employed to mate member 60 with shoulder section 66.

In this version of the invention, the drive shaft 26a is encased within outer tube 22a. Outer tube 22a is formed so that the portion of the tube 22a that subtends relatively flexible tubular member 60 has an inner wall 68 with a diameter greater than that of the diameter of the inner wall that surrounds the rest of drive shaft 26a.

If the above described version of the invention is subjected to side loading, then member 60 will be the primary member that flexes. Since there is a relatively wide interstitial gap between the outer surface of member 60 and the adjacent outer tube inner wall 68, the likelihood of contact between these two surfaces is relatively minimal. Thus, this version of the invention is constructed so that a relatively rigid, efficient cutting surface can be pressed against the tissue. The drive shaft 26a will flex if there is significant side loading so as to avoid failure of this component or the actual cutting head, and in the event there is flexing of the drive shaft, there will be minimal contact between the drive shaft and the outer tube 22a that can inhibit rotation of the drive shaft.

It should, of course, be realized that in other versions of the invention, the member formed of the more flexible metal or metal alloy might not always form the most distal end portion of the drive shaft. In still other versions of the invention, this flexible member may form the portion of the drive shaft that extends from the inner hub. Alternatively, this flexible member may be located at or near the center of the drive shaft. Also, some versions of the invention may have two or more flexible members that form different portions of the drive shaft.

In one or more of the above-described versions of the invention, the individual sections of the drive shaft formed out of the rigid metal or metal alloy may not be physically separate units. In these versions of the invention, one or more small spaced apart webs may extend from the individual sections of the rigid material. These webs are shaped so as to inscribe a circle that has an outer diameter less than the outer diameter of the drive shaft with which they are integral. Once this portion of the drive shaft is formed, bands of the flexible metal or metal alloy are wrapped over each set of webs. These bands thus seal the inside of the drive shaft and provide further means for transferring the torque developed by the drive shaft to its distal end sections. Alternatively, instead of employing webs integral with the workpiece from which the drive shaft rigid sections are formed to interconnect these sections, wire or braid may perform this function. Again, in these versions of the invention, the bands of flexible metal both seal the drive shaft and further transfer the rotational movement of the proximal end of the shaft to the distal end.

In order to perform the above-described torque transfer function, the rigid and flexible sections of the material forming the drive shaft may be formed with interlocking teeth.

Figure 8:
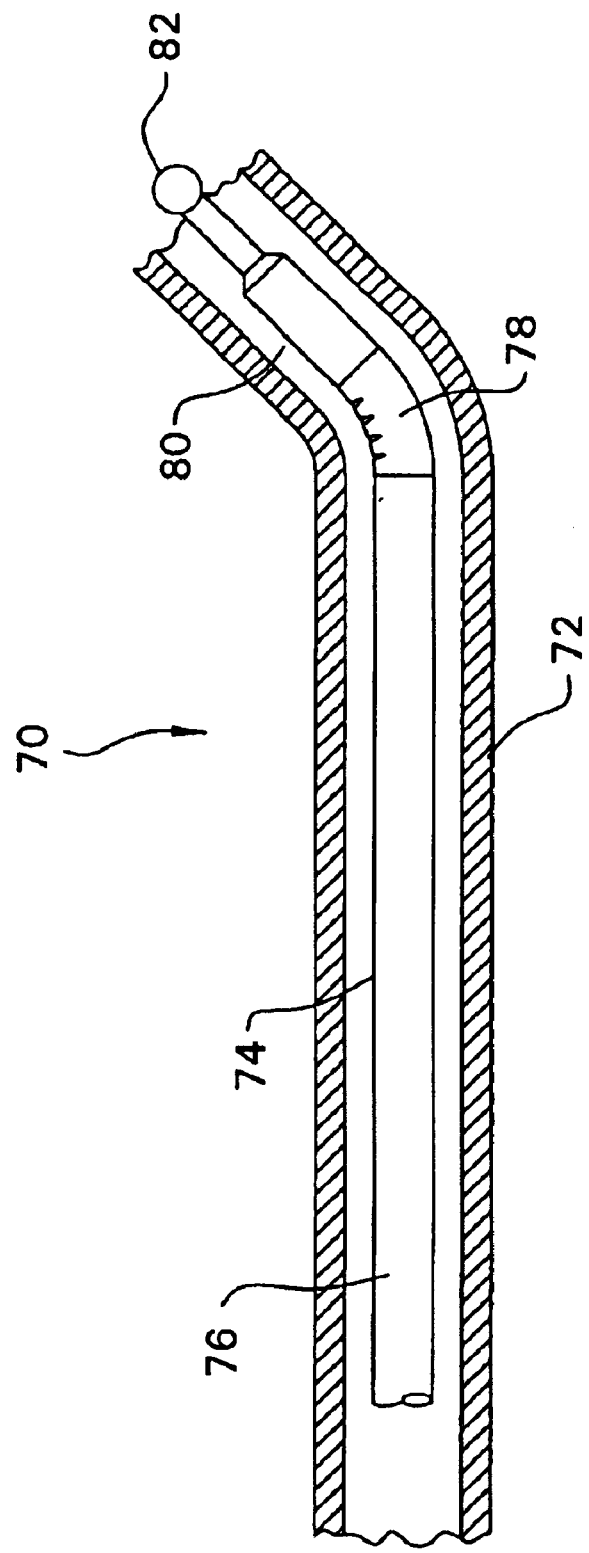
FIG. 8 is a partially cutaway view of the distal end of still another alternative cutting accessory of this invention.

An alternative cutting accessory of this invention may be a bent angle accessory 70 the distal end of which is depicted in FIG. 8. Cutting accessory 70 has a tubular housing 72 that, either during manufacture or post manufacture is bent at a particular angle. Internal to the housing 72 is a drive shaft 74. Drive shaft 74 has a tubular proximal section 76 formed of the relatively inflexible metal or metal alloy. A band or sleeve 78 formed of the more flexible metal or metal alloy is joined to the distal end of section 76. Sleeve 78 is located in the portion of housing 72 that is angled. A drive shaft distal end section 80 is joined to the distal end of sleeve 78. A cutting head, a spherical shaped bur 82 being illustrated by way of example, is attached to the distal end of drive shaft distal end section 80.

Cutting accessory 70 is thus constructed so that sleeve 78, while flexible, is able to transmit torque between the drive shaft sections 76 and 80 and define a portion of the conduit through which suction fluid is drawn towards the proximal end of the cutting accessory. (Proximal end of cutting accessory 70 not shown.) In still other versions of the invention, plural sleeves 78 can be employed to function as the flexible torque-transmitting, conduit-defining members desirable in a bent angled cutting accessory.

Also, in some versions of the invention, it may be desirable to make this flexible section solid. In these versions of the invention, the flexible section is most often located immediately proximal to the actual cutting head. Immediately proximal to this flexible section, the drive shaft is formed with an opening through which fluid and debris are drawn from the surgical site.

Similarly, while the drive shaft of the disclosed version of the invention is formed with a window and is hollow so as to allow a suction to be drawn therethrough, there is no requirement that all versions of the invention be so configured. Furthermore, while it is anticipated that in most versions of the invention, the head will be solid along its length, this need not be a requirement for all versions of the invention. In some versions of the invention the head may be formed with one or more bores. These bores communicate with the center hollow space of the drive shaft to facilitate the drawing of a suction flow through the head.

Also, there is clearly no requirement that all versions of the cutting accessory of this invention have the described outer tube. Just as there is no requirement that the cutting accessory have an outer tube, there is no requirement that, all versions of the invention that are provided with an outer tube have the described mechanism for telescopically retracting the outer tube as the drive shaft and head are pressed into tissue.

It should further be understood that the metals and/or metal alloys from which the drive shaft 26 or 26*a* the head 30 or 30*a* and member 60 of this invention are formed may be different from what has been described. Also, the components of this cutting accessory may be formed from different combinations of material than has been described. For example, it may be desirable to form a cutting accessory with the flexible member 60, the distal end of the drive shaft with steel, and a head formed from Nitinol or other metal or metal allow that has a greater flexibility than the steel.

Moreover, when the flexible metal/metal alloy is used to form a portion of the drive shaft, means different from what has been described may be used to secure together the sleeves of different material that collectively form the drive shaft. For example, these components may be provided with complementary beveled proximally and distally directed surfaces that facilitate their mating. Alternatively, these components may be provided with complementary proximally and distally directed teeth that engage each other.

Thus, it is the object of the appended claims to cover all such variations and modifications that come within the true spirit and scope of this invention.

What is claimed is:

1. A surgical cutting accessory, said cutting accessory comprising:

a drive shaft having opposed proximal and distal ends, said drive shaft being formed from a metal or metal alloy that provides said drive shaft with a first degree of flexibility, said drive shaft having a tubular shape so as to have a hollow space therein and being formed with a window adjacent the distal end of said drive shaft;

a hub integrally attached to the proximal end of said drive shaft, said hub being shaped to couple said drive shaft to a motor and to have an opening that is in communication with the hollow space within said drive shaft; and a head attached to the distal end of said drive shaft to rotate in unison with said drive shaft, said head having a tip that is shaped to have at least one cutting edge, said head being formed from a metal or metal alloy that provides said head with a second degree of flexibility, the second degree of flexibility being greater than the first degree of flexibility.

2. The surgical cutting accessory of claim 1, wherein said head is formed to have a solid stem that is secured to said distal end of said drive shaft.

3. The surgical cutting accessory of claim 1, wherein said head is formed so that the portion of said head that extends from said drive shaft to said tip has a constant diameter and said tip has a diameter less than the diameter of the constant diameter portion.

4. The surgical cutting accessory of claim 1, wherein said hub is a first hub, said accessory further including:

an outer tube disposed over said drive shaft, said outer tube having opposed distal and proximal ends; and a second hub attached to the proximal end of said outer tube.

5. The surgical cutting accessory of claim 1, wherein:

said drive shaft is formed from a metal or metal alloy such that, if said drive shaft is exposed to 1% or more strain, said drive shaft experiences plastic deformation; and said head is formed from a metal or metal alloy so that, if said head is exposed to at least 3% strain, said head recovers the initial shape of said head.

6. The surgical cutting accessory of claim 1, wherein:

said drive shaft is formed from a metal or metal alloy such that, if said drive shaft is exposed to 1% or more strain, said drive shaft experiences plastic deformation; and said head is formed from a metal or metal alloy so that, if said head is exposed to at least 5% strain, said head recovers the initial shape of said head.

7. The surgical cutting accessory of claim 1, wherein said head is formed from a nickel titanium alloy.

8. A surgical cutting accessory, said cutting accessory comprising:

a hub shaped to engage a motor;

an accessory drive shaft that is integrally attached to said hub to rotate in unison with said hub, said drive shaft extending forward from said hub and having a distal end that is spaced from said hub, said drive shaft having a tubular shape defining a hollow space therein and being formed with a window adjacent the distal end thereof, said hub being shaped to have an opening that is in communication with the hollow space within said drive shaft, wherein said drive shaft is formed from steel, the steel providing said drive shaft with a first degree of flexibility; and a head, said head having a stem that extends from the distal end of said drive shaft and is secured to said drive shaft to rotate in unison with said drive shaft and a tip located forward of said drive shaft, said stem of said head being secured to said drive shaft at a location distal from where said window is formed in said drive shaft, said tip being formed with at least one cutting edge, wherein said head is formed from a metal or metal alloy that provides said head with a second degree of flexibility, the second degree of flexibility being greater than the first degree of flexibility.

9. The surgical cutting accessory of claim 8, wherein said head is formed so that said stem has a constant diameter and said tip has a diameter less than the diameter of said stem.

10. The surgical cutting accessory of claim 8, wherein:

said drive shaft is shaped to have a main section with a first constant diameter that extends distally from said first hub, a tapered section with a decreasing diameter located at a distal end of said main section, said window being formed at least partially in said tapered section, and a neck that extends forward from said tapered section; and said stem of said head is fitted in said neck of said drive shaft.

11. The surgical cutting accessory of claim 8, wherein:

the steel from which said drive shaft is formed is such that, if said drive shaft is exposed to 1% or more strain, said drive shaft experiences plastic deformation; and said head is formed from a metal or metal alloy so that, if said head is exposed to at least 3% strain, said head recovers the initial shape of said head.

12. The surgical cutting accessory of claim 8, wherein said head is formed from a nickel titanium alloy.

13. The surgical cutting accessory of claim 8 wherein said hub is a first hub, said accessory further including:

a second hub disposed over the proximal end of said drive shaft; and an outer tube attached to said second hub that extends forward of said second hub to at least partially surround said drive shaft.

14. The surgical cutting accessory of claim 8, wherein said hub is a first hub, said accessory further including:

a second hub disposed over the proximal end of said drive shaft; and an outer tube attached to said second hub that extends over said drive shaft, said outer tube being slidably connected to said second hub and being dimensioned so that, when said outer tube is in a fully extended state relative to said second hub, said outer tube extends over said head.

15. The surgical cutting accessory of claim 8 wherein said hub is a first hub, said accessory further including:

a second hub disposed over the proximal end of said drive shaft;

an outer tube attached to said second hub and extending at least partially over said drive shaft and said drive shaft and said outer tube are collectively dimensioned to define an interstitial space between said drive shaft and said outer tube.

16. A cutting accessory, said accessory comprising:

a hub, said hub being shaped to interlock with an output coupling of a motor to rotate in unison with the output coupling, said hub being shaped to have an opening;

a drive shaft formed of steel and having a hollow tubular shape that is secured to said hub to rotate in unison with said hub, said drive shaft being shaped to have a main section with a first constant diameter, a tapered section at a distal end of said main section of decreasing diameter, a neck at the distal end of said tapered section that has a second diameter less than the first diameter, said drive shaft having a center space that is in communication with the opening of said hub and having a window that is at least partially located in said tapered section wherein, the steel forming said drive shaft provides said drive shaft with a first degree of flexibility; and a cutting head formed from a metal or metal alloy, said cutting head having: a stem that is secured in said neck of said drive shaft so that said cutting head rotates in unison with said drive shaft; and a tip located at the distal end of said cutting head, said tip being shaped to form at least one cutting edge wherein, the metal or metal alloy from which said cutting head is formed provides said cutting head with a second degree of flexibility, the second degree of flexibility being greater than the first degree of flexibility.

17. The cutting accessory of claim 16, wherein said stem of said cutting head has a diameter and said tip has a diameter less than the diameter of said stem.

18. The cutting accessory of claim 16, wherein the portion of said stem of said cutting head that extends from said drive shaft to said tip has a constant diameter.

19. The cutting accessory of claim 16 wherein said hub is a first hub, said accessory further including:

an outer tube disposed over said drive shaft, said outer tube having opposed distal and proximal ends; and a second hub attached to the proximal end of said outer tube.

20. The cutting accessory of claim 16, wherein:

the steel from which said drive shaft is formed is such that, if said drive shaft is exposed to 1% or more strain, said drive shaft experiences plastic deformation; and said head is formed from a metal or metal alloy so that, if said head is exposed to at least 3% strain, said head recovers the initial shape of said head.

21. The cutting accessory of claim 16, wherein said head is formed from a nickel titanium alloy.

22. The cutting accessory of claim 16 wherein said hub is a first hub, said accessory further including:

a second hub disposed over the proximal end of said drive shaft; and an outer tube attached to said second hub that extends over said drive shaft, said outer tube being slidably connected to said second hub and being dimensioned so that, when said outer tube is in a fully extended state relative to said second hub, said outer tube extends over said cutting head.

23. The cutting accessory of claim 16, wherein said hub is a first hub, said accessory further including:
   a second hub disposed over the proximal end of said drive shaft; and
   an outer tube attached to said second hub and extending at least partially over said drive shaft, and said drive shaft and said outer tube are collectively dimensioned to define an interstitial space between said drive shaft and said outer tube.

24. A surgical cutting accessory, said cutting accessory comprising:
   a hub shaped to engage an output coupling of a motor;
   an accessory drive shaft that is tubular and defines a hollow space therein, said drive shaft being integrally attached to said hub to rotate in unison with said hub, said drive shaft extending forward from said hub and having a distal end that is spaced from said hub and a window adjacent said distal end, wherein said drive shaft has at least one first section formed from a metal or metal alloy that provides the at least one first section with a first degree of flexibility and at least one second section formed from a metal or metal alloy that provides the at least one second section with a second degree of flexibility, the second degree of flexibility being greater than the first degree of flexibility, said hub being shaped to have an opening that is in communication with said hollow space of said drive shaft; and
   a head, said head having a stem that is attached to and extends forward from the distal end of said drive shaft and secured to said drive shaft to rotate in unison therewith and a tip located forward of said drive shaft, said tip being formed with at least one cutting edge and said stem being secured to said drive shaft distal from where said window is formed in said drive shaft.

25. The surgical cutting accessory of claim 24, wherein:
   said tip is located at a distal end of said stem and said stem has a constant diameter; and
   said tip has a diameter less than the diameter of said stem.

26. The surgical cutting accessory of claim 24, wherein:
   said drive shaft is shaped to have a main section with a first constant diameter that extends distally from said hub, a tapered section with decreasing diameter located at a distal end of said main section, said window being formed at least partially in said tapered section and communicating with said hollow space of said drive shaft, and a neck that extends forward from said tapered section;
   said hub is formed with an opening that is in communication with the hollow space of said drive shaft; and
   said stem is fitted in said neck of said drive shaft.

27. The surgical cutting accessory of claim 24, wherein the at least one second section of said drive shaft is formed from a nickel titanium alloy.

28. The surgical cutting accessory of claim 24, wherein said head is formed from steel.

29. The surgical cutting accessory of claim 24, wherein said head is formed from a metal or metal alloy that provides said head with a degree of flexibility greater than the first degree of flexibility.

30. The surgical cutting accessory of claim 24 wherein said hub is a first hub, said accessory further including:
   a second hub disposed over the proximal end of said drive shaft; and
   an outer tube attached to said second hub that extends forward of said second hub to at least partially surround said drive shaft.

31. The surgical cutting accessory of claim 24 wherein said hub is a first hub, said accessory further including:
   a second hub disposed over the proximal end of said drive shaft;
   an outer tube attached to said second hub and extending at least partially over said drive shaft and said drive shaft and said outer tube are collectively dimensioned to define an interstitial space between said drive shaft and said outer tube.

32. A surgical cutting accessory comprising:
   a drive shaft having opposed proximal and distal ends, said drive shaft being formed from a metal or metal alloy that provides said drive shaft with a first degree of flexibility;
   a first hub integrally attached to the proximal end of said drive shaft, said first hub being shaped to couple said drive shaft to a motor;
   a head attached to the distal end of said drive shaft to rotate in unison with said drive shaft, said head having a tip that is shaped to have at least one cutting edge, said head being formed from a metal or metal alloy that provides said head with a second degree of flexibility, the second degree of flexibility being greater than the first degree of flexibility;
   a second hub disposed over the proximal end of said drive shaft; and
   an outer tube attached to said second hub that extends over said drive shaft, said outer tube being slidably connected to said second hub and being dimensioned so that, when said outer tube is in a fully extended state relative to said second hub, said outer tube extends over said head.

33. The surgical cutting accessory of claim 32, wherein said drive shaft has a tubular shape defining a hollow space therein and defines a window adjacent said distal end thereof which communicates with said hollow space, said first hub having an opening in communication with said hollow space of said drive shaft.

34. The surgical cutting accessory of claim 32, wherein said outer tube is biased into the fully extended state by a biasing member and telescopes inwardly relative to said second hub in opposition to the force exerted by said biasing member as said head and said drive shaft are advanced into tissue to cut same.

35. A surgical cutting accessory comprising:
   a drive shaft having opposed proximal and distal ends, said drive shaft being formed from a metal or metal alloy that provides said drive shaft with a first degree of flexibility;
   a first hub integrally attached to the proximal end of said drive shaft, said first hub being shaped to couple said drive shaft to a motor;
   a head attached to the distal end of said drive shaft to rotate in unison with said drive shaft, said head having a tip that is shaped to have at least one cutting edge, said head being formed from a metal or metal alloy that provides said head with a second degree of flexibility, the second degree of flexibility being greater than the first degree of flexibility;

a second hub disposed over the proximal end of said drive shaft; and an outer tube attached to said second hub and extending at least partially over said drive shaft, and said drive shaft and said outer tube are collectively dimensioned to define an interstitial space between said drive shaft and said outer tube.

36. A surgical cutting accessory, said cutting accessory comprising:

a hub shaped to engage an output coupling of a motor;

an accessory drive shaft that is integrally attached to said hub to rotate in unison with said hub, said drive shaft extending forward from said hub and having a distal end that is spaced from said hub, wherein said drive shaft has at least one first section formed from a metal or metal alloy that provides the at least one first section with a first degree of flexibility and at least one second section formed from a metal or metal alloy that provides the at least one second section with a second degree of flexibility, the second degree of flexibility being greater than the first degree of flexibility; and a head, said head having a stem of a constant diameter that is attached to and extends forward from the distal end of said drive shaft and is secured to said drive shaft to rotate in unison therewith, and a tip located forward of said drive shaft at a distal end of said stem, said tip being formed with at least one cutting edge and a diameter less than the diameter of said stem.

37. A surgical cutting accessory, said cutting accessory comprising:

a hub shaped to engage an output coupling of a motor and having an opening therein;

an accessory drive shaft that is integrally attached to said hub to rotate in unison with said hub, said drive shaft being tubular and defining a hollow space therein in communication with said opening of said hub, said drive shaft extending forward from said hub and having a distal end that is spaced from said hub, wherein said drive shaft has at least one first section formed from a metal or metal alloy that provides the at least one first section with a first degree of flexibility and at least one second section formed from a metal or metal alloy that provides the at least one second section with a second degree of flexibility, the second degree of flexibility being greater than the first degree of flexibility, said drive shaft being shaped to have a main section with a first constant diameter that extends distally from said hub, a tapered section with a decreasing diameter located at a distal end of said main section, a window formed at least partially in said tapered section, and a neck that extends forward from said tapered section; and a head, said head having a stem that extends forward from and is fitted in said neck of said drive shaft, said stem being secured to said drive shaft to rotate in unison therewith, and a tip located forward of said stem, said tip formed with at least one cutting edge.

38. The surgical cutting accessory of claim 37, wherein said main section comprises said first section, and said second section is disposed between said main section and said tapered section.

39. A surgical cutting accessory, said cutting accessory comprising:

a hub shaped to engage an output coupling of a motor;

an accessory drive shaft that is integrally attached to said hub to rotate in unison with said hub, said drive shaft extending forward from said hub and having a distal end that is spaced from said hub, wherein said drive shaft has at least one first section formed from a metal or metal alloy that provides the at least one first section with a first degree of flexibility and at least one second section formed from a metal or metal alloy that provides the at least one second section with a second degree of flexibility, the second degree of flexibility being greater than the first degree of flexibility; and a head formed from steel, said head being attached to and extending forward from the distal end of said drive shaft and secured to said drive shaft to rotate in unison with said drive shaft and a tip located forward of said drive shaft, said tip being formed with at least one cutting edge.

40. The surgical cutting accessory of claim 39, wherein said first section is formed from steel, and said second section is formed from a nickel titanium alloy and is disposed between said first section and said head.

41. A surgical cutting accessory, said cutting accessory comprising:

a first hub shaped to engage an output coupling of a motor;

an accessory drive shaft that is integrally attached to said first hub to rotate in unison with said first hub, said drive shaft extending forward from said first hub and having a distal end that is spaced from said first hub, wherein said drive shaft has at least one first section formed from a metal or metal alloy that provides the at least one first section with a first degree of flexibility and at least one second section formed from a metal or metal alloy that provides the at least one second section with a second degree of flexibility, the second degree of flexibility being greater than the first degree of flexibility;

a head, said head being attached to and extending forward from the distal end of said drive shaft and secured to said drive shaft to rotate in unison with said drive shaft and a tip located forward of said drive shaft, said tip being formed with at least one cutting edge;

a second hub disposed over the proximal end of said drive shaft; and an outer tube attached to said second hub and extending forward of said second hub to at least partially surround said drive shaft.

42. A surgical cutting accessory, said cutting accessory comprising:

a first hub shaped to engage an output coupling of a motor;

an accessory drive shaft that is integrally attached to said first hub to rotate in unison with said first hub, said drive shaft extending forward from said first hub and having a distal end that is spaced from said first hub, wherein said drive shaft has at least one first section formed from a metal or metal alloy that provides the at least one first section with a first degree of flexibility and at least one second section formed from a metal or metal alloy that provides the at least one second section with a second degree of flexibility, the second degree of flexibility being greater than the first degree of flexibility;

a head, said head being attached to and extending forward from the distal end of said drive shaft and secured to said drive shaft to rotate in unison with said drive shaft and a tip located forward of said drive shaft, said tip formed with at least one cutting edge;

a second hub disposed over the proximal end of said drive shaft; and an outer tube attached to said second hub and extending at least partially over said drive shaft, said outer tube and said drive shaft being collectively dimensioned to define an interstitial space between said drive shaft and said outer tube.

43. A surgical cutting accessory, said cutting accessory comprising:

a drive shaft having opposed proximal and distal ends, said drive shaft being formed from a metal or metal alloy that provides said drive shaft with a first degree of flexibility;

a first hub integrally attached to the proximal end of said drive shaft, said first hub being shaped to couple said drive shaft to a motor; and a head attached to the distal end of said drive shaft to rotate in unison with said drive shaft, said head having a tip that is shaped to have at least one cutting edge, said head being formed from a metal or metal alloy that provides said head with a second degree of flexibility, the second degree of flexibility being greater than the first degree of flexibility, wherein said head has a portion of a constant diameter which extends from said drive shaft to said tip, and said tip has a diameter less than the diameter of said constant diameter portion.

* * * * *

UNITED STATES PATENT AND TRADEMARK OFFICE
CERTIFICATE OF CORRECTION

PATENT NO.    : 6,824,552 B2
DATED         : November 30, 2004
INVENTOR(S)   : Braden M. Robison et al.

It is certified that error appears in the above-identified patent and that said Letters Patent is hereby corrected as shown below:

<u>Title page,</u>
Item [75], change "[75] Inventors: Braden M. Robison, Fremont, CA (US); Nathan A. Swain, Sunnyvale, CA (US)" to -- [75] Inventors: Braden M. Robison, Fremont, CA (US); Nathan A. Swain, Sunnyvale, CA (US); Kurt M. Deutmeyer, San Jose, CA (US) --.

Signed and Sealed this

Eighteenth Day of April, 2006

JON W. DUDAS
*Director of the United States Patent and Trademark Office*